US008228060B2

(12) United States Patent
Busse (10) Patent No.: US 8,228,060 B2
(45) Date of Patent: Jul. 24, 2012

(54) METHOD AND APPARATUS FOR GENERATING A FLIP ANGLE SCHEDULE FOR A SPIN ECHO TRAIN PULSE SEQUENCE

(75) Inventor: Reed F. Busse, Madion, WI (US)

(73) Assignee: General Electric Company, Schenectady, NY (US)

( * ) Notice: Subject to any disclaimer, the term of this patent is extended or adjusted under 35 U.S.C. 154(b) by 1149 days.

(21) Appl. No.: 11/767,903

(22) Filed: Jun. 25, 2007

(65) Prior Publication Data

US 2008/0319301 A1 Dec. 25, 2008

(51) Int. Cl.
*G01V 3/00* (2006.01)
(52) U.S. Cl. .......................... 324/307; 324/309; 324/314
(58) Field of Classification Search .......... 324/300–322; 600/407–427; 382/128–131
See application file for complete search history.

(56) References Cited

U.S. PATENT DOCUMENTS

| | | | | |
|---|---|---|---|---|
| 5,315,249 | A * | 5/1994 | Le Roux et al. | 324/309 |
| 5,345,176 | A * | 9/1994 | LeRoux et al. | 324/309 |
| 5,410,249 | A * | 4/1995 | Van Yperen et al. | 324/309 |
| 6,230,039 | B1 * | 5/2001 | Stuber et al. | 600/410 |
| 6,265,875 | B1 * | 7/2001 | Saranathan et al. | 324/314 |
| 6,489,766 | B1 * | 12/2002 | Alsop | 324/313 |
| 6,850,063 | B2 * | 2/2005 | Hennig | 324/314 |
| 6,850,083 | B2 | 2/2005 | Leshnovolsky et al. | |
| 6,956,374 | B2 * | 10/2005 | Busse | 324/314 |
| 7,164,268 | B2 * | 1/2007 | Mugler | 324/307 |
| 7,800,368 | B2 * | 9/2010 | Vaughan et al. | 324/318 |
| 8,040,135 | B1 * | 10/2011 | Cukur et al. | 324/309 |
| 2003/0112008 | A1 * | 6/2003 | Hennig | 324/314 |
| 2005/0001617 | A1 * | 1/2005 | Busse | 324/307 |
| 2008/0129298 | A1 * | 6/2008 | Vaughan et al. | 324/322 |
| 2008/0319301 | A1 * | 12/2008 | Busse | 600/410 |
| 2009/0033328 | A1 * | 2/2009 | Feiweier | 324/309 |
| 2009/0105582 | A1 * | 4/2009 | Dougherty et al. | 600/420 |
| 2011/0044524 | A1 * | 2/2011 | Wang et al. | 382/131 |
| 2011/0181282 | A1 * | 7/2011 | Dannels | 324/309 |

OTHER PUBLICATIONS

Hennig J , Multiecho Imaging Sequences with Low Refocusing Flip Angles, Journal of Magnetic Resonance, 78:397-407 (1988).
Hennig J , Echoes—How to Generate, Recognize, Use or Avoid Them in MR Imaging Sequences, Concepts in Magnetic Resonance ; 3:125-143 (1991).
Leroux P, Hinks RS, Stabilization of Echo Amplitudes in FSE Sequences, Magnetic Resonance in Medicine ; 30:183-191 (1993).

(Continued)

*Primary Examiner* — Melissa Koval
*Assistant Examiner* — Tiffany Fetzner
(74) *Attorney, Agent, or Firm* — The Small Patent Law Group; Dean D. Small (57) ABSTRACT

A method for calculating a flip angle schedule for a train of refocusing radio frequency (RF) pulses with reduced flip angles allows control of RF power deposition and use of a longer echo train. A target signal is defined for each echo in the echo train, and flip angles are then calculated from the target signals. The target signal schedule includes two phases. In the first phase, the target signals drop asymptotically to efficiently establish a pseudo-steady state at a pre-defined minimum signal level, $S_{min}$. In the second phase, the target signal is increased monotonically for the remainder of the train to a pre-defined maximum signal level, $S_{max}$. By increasing the target signal, the effect of relaxation may be reduced, decreasing blurring and ringing artifacts. Flip angles are then calculated from the target signal schedule, using a simplified method that requires no information about the tissues' relaxation properties.

20 Claims, 7 Drawing Sheets

OTHER PUBLICATIONS

Schaeffter T, Boernert P, Leibfritz D, PSF Improvements in Single Shot GRASE Imaging, Proc SMR; San Francisco. p. 27 (1994).

ALSOP DC, The Sensitivity of Low Flip Angle RARE Imaging, Magnetic Resonance in Medicine ; 37:176-184 (1997).

Mugler JP, Kiefer B, Brookeman Jr, Three-Dimensional T2-Weighted Imaging of the Brain Using Very Long Spin-Echo Trains, Proc ISMRM; Denver. p. 687 (2000).

Busse RF, Riederer SJ, Reducing SAR in Real-Time SSFSE Imaging with Variable-Flip Hard Refocusing RF Pulses, Proc ISMRM; Glasgow. p. 1790 (2001).

Hennig J, Weigel M, Scheffler K, Multiecho Sequences With Variable Refocusing Flip Angles: Optimization of Signal Behavior Using Smooth Transitions Between Pseudo Steady States (TRAPS), Magnetic Resonance in Medicine ; 49:527-535 (2003).

Mugler JP, Meyer H, Kieffer B, Practical Implennentaion of Optimized Tissue-Specific Prescribed Signal Evolutions for Improved Turbo-Spin-Echo Imaging, Proc ISMRM; Toronto. p. 203 (2003).

Busse RF, Zur Y, Li X, Body Imaging at 3T: Lower SAR Yields Improved Coverage with VERSE and Modulated Angle Refocusing Trains, Proc ISMRM; Toronto. p. 206 (2003).

Busse RF, Reduced RF Power Without Blurring: Correcting for Modulation of Refocusing Flip Angle in FSE Sequences, Magnetic Resonance in Medicine ; 51:1031-1037 (2004).

Hennig J, Calculation of Flip Angles for Echo Trains with Predefined Amplitudes with the Extended Phase Graph (EPG)-Algorithm: Principles and Applications to Hyperecho and TRAPS Sequences, Magnetic Resonance in Medicine ; 51:68-80 (2004).

Busse RF, Hariharan H, Vu A, Brittain JH, Fast Spin Echo Sequences with Very Long Echo Trains: Design of Variable Refocusing Flip Angle Schedules and Generation of Clinical T2 Contrast, Magnetic Resonance in Medicine ; 55:1030-1037 (2006).

Busse, RF, Equivalent T2-Contrast for Fast Spin Echo Sequences with Low and Variable Flip Refocusing, International Society of Magnetic Resonance in Medicine, 2005 Scientific Program, 2005, Miami.

Busse, RF, Designing Variable Flip Angle Refocusing Trains to Optimize Resolution, Signal-to-Noise, and RF Power, International Society of Magnetic Resonance in Medicine, 2005 Scientific Program, 2005, Miami.

* cited by examiner

METHOD AND APPARATUS FOR GENERATING A FLIP ANGLE SCHEDULE FOR A SPIN ECHO TRAIN PULSE SEQUENCE

TECHNICAL FIELD

The present invention relates generally to magnetic resonance imaging (MRI) systems and, in particular, to a method and apparatus for generating a flip angle schedule for a spin echo train pulse sequence with reduced refocusing flip angles where the spin echo train pulse sequence may be used to acquire images.

BACKGROUND

Magnetic resonance imaging (MRI) is a medical imaging modality that can create pictures of the inside of a human body without using x-rays or other ionizing radiation. MRI uses a powerful magnet to create a strong, uniform, static magnetic field (i.e., the "main magnetic field"). When a human body, or part of a human body, is placed in the main magnetic field, the nuclear spins that are associated with the hydrogen nuclei in tissue water become polarized. This means that the magnetic moments that are associated with these spins become preferentially aligned along the direction of the main magnetic field, resulting in a small net tissue magnetization along that axis (the "z axis," by convention). A MRI system also comprises components called gradient coils that produce smaller amplitude, spatially varying magnetic fields when current is applied to them. Typically, gradient coils are designed to produce a magnetic field component that is aligned along the z axis (i.e., the "longitudinal axis") and that varies linearly in amplitude with position along one of the x, y or z axes. The effect of a gradient coil is to create a small ramp on the magnetic field strength and concomitantly on the resonance frequency of the nuclear spins, along a single axis. Three gradient coils with orthogonal axes are used to "spatially encode" the MR signal by creating a signature resonance frequency at each location in the body. Radio frequency (RF) coils are used to create pulses of RF energy at or near the resonance frequency of the hydrogen nuclei. These coils are used to add energy to the nuclear spin system in a controlled fashion. As the nuclear spins then relax back to their rest energy state, they give up energy in the form of an RF signal. This signal is detected by the MRI system and is transformed into an image using a computer and known reconstruction methods.

MR images may be created by applying currents to the gradient and RF coils according to known methods called "pulse sequences". A pulse sequence diagram may be used to show the amplitude, phase and timing of the various current pulses applied to the gradient and RF coils for a given pulse sequence. A system operator's selection of a pulse sequence determines the relative appearance of different tissue types in the resultant images, emphasizing or suppressing tissue types as desired. The inherent MR properties of tissue, most commonly the relaxation times T1 and T2, may be exploited to create images with a desirable contrast between different tissues. For example, in a MR image of a brain, gray matter may be caused to appear either darker or lighter than white matter according to the MRI system operator's choice of a T1-weighted or T2-weighted pulse sequence.

Spin Echo (SE) pulse sequences have been used extensively in clinical MR imaging, in part because of their robustness to off-resonance effects such as are caused by main magnetic field inhomogeneity or magnetic susceptibility variations in the imaging subjects. A Spin Echo pulse sequence includes an excitation RF pulse and a single refocusing RF pulse. Typically, the flip angles of the excitation and refocusing pulses are set to 90° and 180° respectively. A spin echo, formed by the refocusing RF pulse, is encoded as a single k-space line and collected at time TE, the "echo time," after the excitation RF pulse. This combination of pulses and echo acquisitions is repeated at time interval TR, the "repetition time," until all necessary lines of k-space have been collected. The main advantage of a SE pulse sequence is its ability to create a specific contrast weighting, either T1-, T2-, or proton density-weighted, by modifying the TE and TR.

Fast Spin Echo (FSE) (also known in the art as "Rapid Acquisition Relaxation Enhancement (RARE)," or "Turbo Spin Echo (TSE)") is a fast version of a SE sequence that uses an excitation RF pulse followed by a train of refocusing RF pulses and resulting spin echoes (i.e., a resulting "echo train"). Typically, the flip angles of the excitation and refocusing RF pulses are set to 90° and 180°, respectively. Multiple spin echoes are collected after each excitation RF pulse, i.e., multiple k-space lines are obtained in a single TR. FSE may be used in either two-dimensional (2D) or three-dimensional (3D) acquisition mode. The maximum practical length of the echo train, i.e., the "Echo Train Length" (ETL), is determined primarily by the T2 relaxation times of the tissues being imaged and the maximum allowable RF power deposition. At 1.5 Tesla, the length of a train of 180° refocusing RF pulses is limited practically to less than approximately 300 ms by the "T2 decay envelope" of the amplitude of the echoes. Typically, TR is significantly longer than TE in order to allow sufficient longitudinal recovery (i.e., "T1 recovery") of the magnetization after an echo train and before the next excitation. Two-dimensional acquisitions use an interleaving strategy in which k-space data from multiple slices are acquired during a single TR. This acquisition strategy is typically very efficient. Each TR may be partitioned into data acquisition periods for multiple slices, eliminating dead time in the TR. For 3D acquisitions, however, an interleaving strategy is not possible because the entire volume of interest is excited and significant dead time results between the end of an echo train and the next excitation RF pulse.

Refocusing RF pulses with reduced or smaller (i.e., less than 180°) flip angles have been used to reduce RF power deposition and to prolong the amount of time for which magnetization is available for refocusing. The use of reduced flip angles results in the temporary storage of magnetization in stimulated echo coherence pathways during which time the magnetization decays at the tissue's T1 relaxation rate instead of the T2 relaxation rate. Because T1 is significantly longer than T2 for most tissues, the use of refocusing RF pulses with smaller flip angles increases the amount of magnetization available for creating echoes later in the echo train and echo train lengths may be increased while maintaining signal. It is not necessary, however, for all the refocusing RF pulses to have the same flip angle. Rather, a "flip angle schedule" specifying the individual flip angles in a train of RF pulses may be devised to control the RF power deposition and to control aspects of the image appearance such as image contrast, signal-to-noise ratio, blurring, and spatial resolution. For example, instead of using a constant smaller flip angle throughout the RF pulse train, the flip angles of the first refocusing RF pulses may be decreased from a large flip angle to the desired smaller flip angle gradually such that the resultant echoes vary smoothly in magnitude and image artifacts from signal oscillations are eliminated. This preparatory stage in which the flip angles are gradually decreased serves to create a "pseudo-steady state" of the magnetization, in which the resultant echo magnitudes are constant (excluding the effects of relaxation). Flip angles for later refocusing RF pulses in the RF pulse train may be varied to increase the amount of magnetization stored in stimulated echo pathways, thereby maintaining the magnitude of echoes in the echo train and offsetting the effects of T2 relaxation. This allows the use of longer echo trains.

Accordingly, it would be desirable to provide a method and apparatus for calculating or generating a flip angle schedule for long spin echo train pulse sequences with reduced refocusing flip angles. It would be advantageous to provide a method for generating a flip angle schedule that is efficient and that is generally applicable across various tissues and materials (i.e., a method that does not need to be tailored to tissue specific relaxation parameters).

BRIEF DESCRIPTION OF THE INVENTION

In accordance with an embodiment, a method for calculating a flip angle schedule for a spin echo train with reduced refocusing flip angles, the spin echo train having a plurality of spin echoes, includes defining a target signal schedule including target signals for each spin echo in the spin echo train, the target signal schedule including a first phase configured to establish a pseudo-steady state and a second phase where the target signals increase from a pre-defined minimum signal value to a pre-defined maximum signal value, and calculating a corresponding flip angle schedule from the target signal schedule using only non-relaxation properties.

In accordance with another embodiment, a method for acquiring magnetic resonance images using a spin echo train with reduced refocusing flip angles, the spin echo train having a plurality of spin echoes, includes applying a magnetic field to an imaging subject comprising tissues, to cause a net longitudinal magnetization in the tissues, defining a target signal schedule including target signals for each spin echo in the spin echo train, the target signal schedule including a first phase configured to establish a pseudo-steady state and a second phase where the target signals increase from a pre-defined minimum signal value to a pre-defined maximum signal value, calculating a corresponding flip angle schedule from the target signal schedule using only non-relaxation properties, generating an excitation radio frequency pulse, generating a plurality of refocusing radio frequency pulses, each refocusing radio frequency pulse having a flip angle determined based on the flip angle schedule, and acquiring magnetic resonance imaging data.

In accordance with another embodiment, a computer-readable medium having computer-executable instructions for performing a method for calculating a flip angle schedule for a spin echo train with reduced refocusing flip angles, the spin echo train having a plurality of spin echoes, includes program code for defining a target signal schedule including target signals for each spin echo in the spin echo train, the target signal schedule including a first phase configured to establish a pseudo-steady state and a second phase where the target signals increase from a pre-defined minimum signal value to a pre-defined maximum signal value, and program code for calculating a corresponding flip angle schedule from the target signal schedule using only non-relaxation properties.

In accordance with another embodiment, an apparatus for acquiring magnetic resonance images using a spin echo train with reduced refocusing flip angles, the spin echo train having a plurality of spin echoes, includes a magnetic resonance imaging assembly including a magnet, a plurality of gradient coils, a radio frequency coil, a radio frequency transceiver system, and a pulse generator module, and a computer system coupled to the magnetic resonance imaging assembly and programmed to define a target signal schedule including target signals for each spin echo in the spin echo train, the target signal schedule including a first phase configured to establish a pseudo-steady state and a second phase where the target signals increase from a pre-defined minimum signal value to a pre-defined maximum signal value, calculate a corresponding flip angle schedule from the target signal schedule using only non-relaxation properties, generate an excitation radio frequency pulse, generate a plurality of refocusing radio frequency pulses, each refocusing radio frequency pulse having a flip angle determined based on the flip angle schedule, and acquire magnetic resonance imaging data.

BRIEF DESCRIPTION OF THE DRAWINGS

Embodiments are illustrated by way of example and not limitation in the figures of the accompanying drawings, in which like reference numerals indicate corresponding, analogous or similar elements, and in which.

DETAILED DESCRIPTION

In the following detailed description, numerous specific details are set forth in order to provide a thorough understanding of embodiments. However it will be understood by those of ordinary skill in the art that the embodiments may be practiced without these specific details. In other instances, well-known methods, procedures, components and circuits have not been described in detail so as not to obscure the embodiments.

A flip angle schedule for a train of refocusing radio frequency (RF) pulses may be used to control RF power deposition and signal amplitudes for an echo train pulse sequence with reduced (i.e., less than 180°) flip angles. A target "signal" (i.e., signal level or echo magnitude) is defined for each echo in the echo train (e.g., via a target signal schedule) and flip angles are then calculated from the target signals. The target signal schedule includes two phases. In a first phase (Phase I), the target signals drop asymptotically to efficiently establish a pseudo-steady state at a pre-defined minimum signal level, $S_{min}$. In a second phase (Phase II), the target signals are increased monotonically for the remainder of the train of RF refocusing pulses to a pre-defined maximum signal level, $S_{max}$. By increasing the target signals, the effects of relaxation may be reduced and therefore blurring and ringing artifacts in the images may be decreased. Flip angles for a "flip angle schedule" are then calculated from the target signal schedule, using a simplified method that uses only non-relaxation properties or parameters. As used herein, the term non-relaxation properties or parameters refers to properties other than the tissue/material specific relaxation parameters T1 and T2.

Use of reduced flip angles results in a mixed T1/T2 contrast in images, due to the stimulated echo contribution. Calculations to determine the mixed T1/T2 decay rate are used to find an equivalent echo time ($TE_{equiv}$) for each echo in the train. $TE_{equiv}$ describes the image contrast weighting that would be obtained if that echo were used to fill the center of k-space expressed in terms of an equivalent TE from a conventional sequence that uses only 180° refocusing RF pulses. Contrast weighting from a conventional 180° sequence is familiar to most system operators and therefore the use of a $TE_{equiv}$ allows a system operator to select a TE as though he/she were prescribing a conventional sequence.

Figure 1:
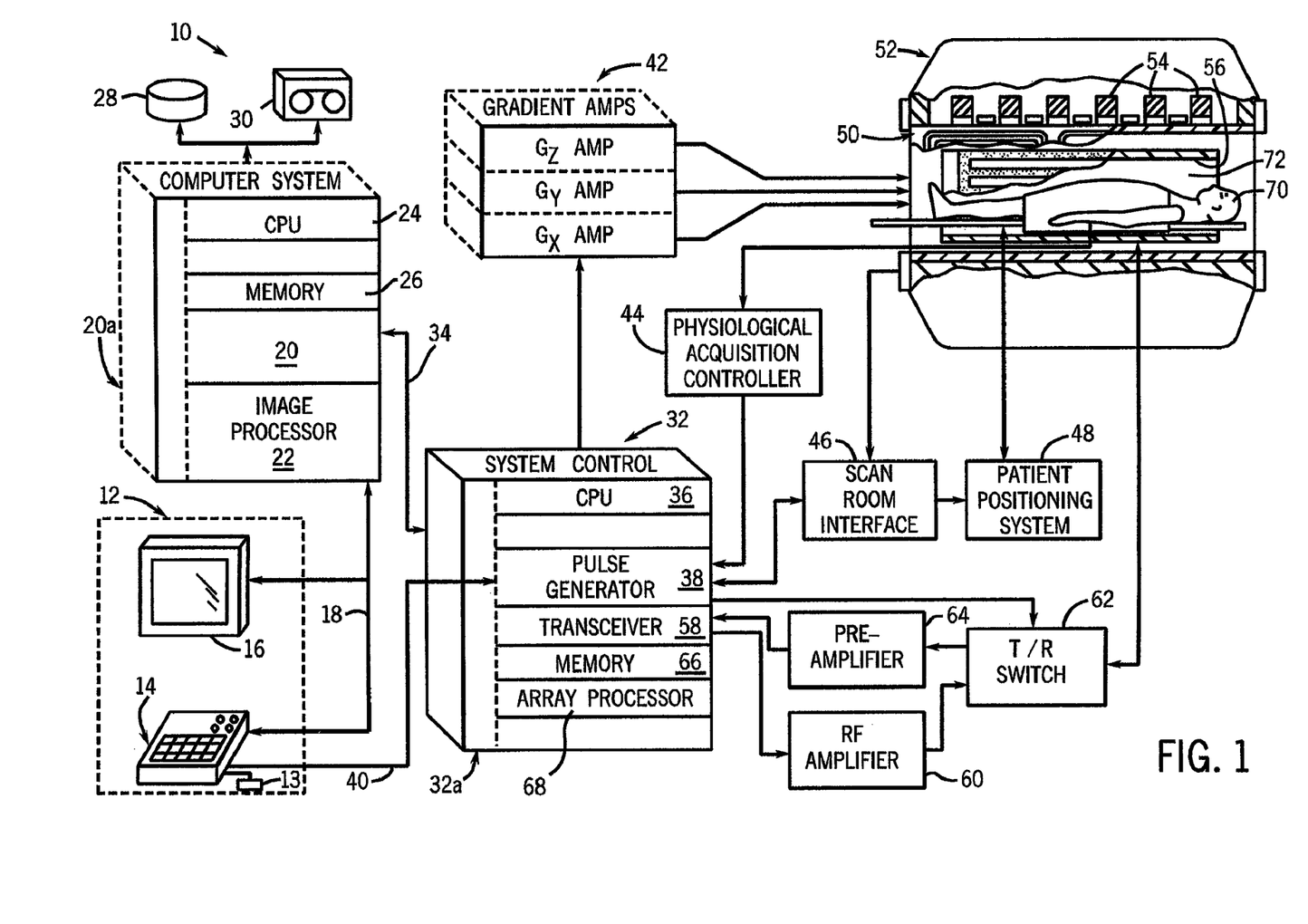
FIG. 1 is a schematic block diagram of an exemplary magnetic resonance imaging system in accordance with an embodiment.

FIG. 1 is a schematic block diagram of an exemplary magnetic resonance imaging system in accordance with an embodiment. The operation of MRI system 10 is controlled from an operator console 12 that includes a keyboard or other input device 13, a control panel 14, and a display 16. The console 12 communicates through a link 18 with a computer system 20 and provides an interface for an operator to prescribe MRI scans, display the resultant images, perform image processing on the images, and archive data and images. The computer system 20 includes a number of modules that communicate with each other through electrical and/or data connections, for example such as are provided by using a backplane 20a. Data connections may be direct wired links or may be fiber optic connections or wireless communication links or the like. The modules of computer system 20 may include an image processor module 22, a CPU module 24 and a memory module 26 that may include a frame buffer for storing image data arrays. In an alternative embodiment, the image processor module 22 may be replaced by image processing functionality on the CPU module 24. The computer system 20 is linked to archival media devices, such as disk storage 28 and tape drive 30 for storage of image data and programs, and communicates with a separate system control computer 32 through a link 34. Archival media include, but are not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which may be used to store the desired instructions and which can be accessed by computer system 20, including by internet or other computer network forms of access. The input device 13 can include a mouse, joystick, keyboard, track ball, touch activated screen, light wand, voice control, or any similar or equivalent input device and may be used for interactive geometry prescription.

The system control computer 32 includes a set of modules in communication with each other via electrical and/or data connections 32a. Data connections 32a may be direct wired links or may be fiber optic connections or wireless communication links or the like. In alternative embodiments, the modules of computer system 20 and system control computer 32 may be implemented on the same computer systems or a plurality of computer systems. The modules of system control computer 32 include a CPU module 36 and a pulse generator module 38 that connects to the operator console 12 through a communications link 40. The pulse generator module 38 may alternatively be integrated into the scanner equipment (e.g., magnet assembly 52). It is through link 40 that the system control computer 32 receives commands from the operator to indicate the scan sequence that is to be performed. The pulse generator module 38 operates the system components that play out (i.e., perform) the desired pulse sequence and produces data called RF waveforms which control the timing, strength and shape of the RF pulses to be used and the timing and length of the data acquisition window. The pulse generator module 38 connects to a gradient amplifier system 42 and produces data called gradient waveforms which control the timing and shape of the gradient pulses that are to be used during the scan. The pulse generator module 38 may also receive patient data from a physiological acquisition controller 44 that receives signals from a number of different sensors connected to the patient, such as ECG signals from electrodes attached to the patient. The pulse generator module 38 connects to a scan room interface circuit 46 that receives signals from various sensors associated with the condition of the patient and the magnet system. It is also through the scan room interface circuit 46 that a patient positioning system 48 receives commands to move the patient table to the desired position for the scan.

The gradient waveforms produced by the pulse generator module 38 are applied to gradient amplifier system 42 which is comprised of Gx, Gy and Gz amplifiers. Each gradient amplifier excites a corresponding physical gradient coil in a gradient coil assembly generally designated 50 to produce the magnetic field gradient pulses used for spatially encoding acquired signals. The gradient coil assembly 50 forms part of a magnet assembly 52 that includes a polarizing magnet 54 and a whole-body RF coil 56. A patient or imaging subject 70 may be positioned within a cylindrical patient imaging volume 72 of the magnet assembly 52. A transceiver module 58 in the system control computer 32 produces pulses that are amplified by an RF amplifier 60 and coupled to the RF coils 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered and digitized in the receiver section of the transceiver 58. The transmit/receive switch 62 is controlled by a signal from the pulse generator module 38 to electrically connect the RF amplifier 60 to the RF coil 56 during the transmit mode and to connect the preamplifier 64 to the coil during the receive mode. The transmit/receive switch 62 can also enable a separate RF coil (for example, a surface coil) to be used in either the transmit or receive mode.

The MR signals sensed by the RF coil 56 are digitized by the transceiver module 58 and transferred to a memory module 66 in the system control computer 32. MRI data is typically collected in a Fourier space known in imaging as "k-space," a reciprocal space connected to real space via a Fourier transform. Each MR signal is encoded with a particular spatial frequency using "phase-encoding" gradient pulses, and multiple such MR signals are digitized and stored in k-space for later reconstruction as an image. Typically, frames of data corresponding to MR signals are stored temporarily in the memory module 66 until they are subsequently transformed to create images. An array processor 68 uses a known transformation method, most commonly a Fourier transform, to create images from the MR signals. These images are communicated through the high speed link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on display 16.

Figure 2:
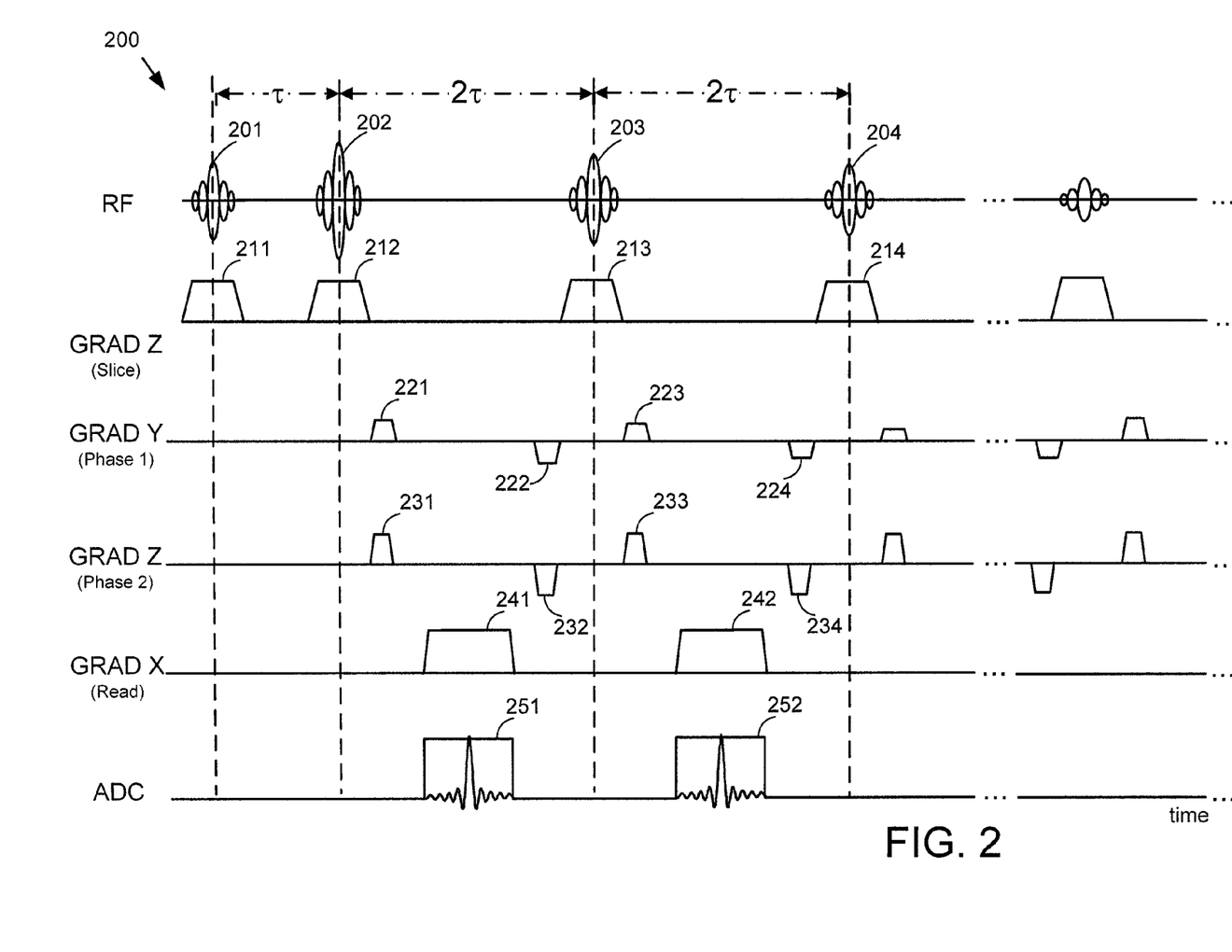
FIG. 2 shows a diagram of a 3D FSE pulse sequence for a single repetition time (TR) in accordance with an embodiment.

In an exemplary embodiment, a three-dimensional (3D) Fast Spin Echo (FSE) pulse sequence with reduced refocusing RF pulse flip angles may be used to acquire k-space data. FIG. 2 shows a diagram of a 3D FSE pulse sequence for a single repetition time (TR) in accordance with an embodiment. The FSE sequence depicted in FIG. 2 is compatible with the above-described MRI system of FIG. 1 or any similar or equivalent system for obtaining MR images. The 3D FSE sequence 200 collects multiple k-space encoded echoes 251, 252 (additional echoes not shown) in a single TR. The sequence 200 begins with an excitation RF pulse 201 (typically a 90 degree RF pulse) played simultaneously with a slab-selective gradient pulse 211 which tips a portion of the longitudinal magnetization into the transverse plane. At a time interval, τ, after the excitation pulse, a first refocusing RF pulse 202 and slab-selective gradient pulse 212 cause the transverse magnetization in a slab to refocus as a first spin echo 251. The first spin echo 251 is "phase-encoded" using a first phase-encoding gradient pulse 221 along the logical y-direction. It is also "slice-encoded" using a second phase-encoding gradient pulse 231 along the logical z-direction and it is read out using a "read-out" gradient pulse 241. In one embodiment, phase-encoding during the echo train is performed by stepping the amplitude of each phase-encoding gradient such that the k-space encoding steps through $k_y$ in a linear fashion and slice-encoding is performed using a single slice-encoding gradient amplitude for the entire echo train and stepping the slice-encoding gradient amplitude for subsequent TRs. After read-out, the phase-encoding is rewound using a phase rewinder gradient pulse 222 that has the same amplitude but negative polarity compared to the phase-encoding gradient 221 and the slice-encoding is similarly rewound using a slice rewinder gradient pulse 232.

At a time interval, 2τ, after the first refocusing pulse 202, a second refocusing RF pulse 203 and slice-select gradient pulse 213 cause the transverse magnetization to refocus a second time as a second spin echo 252. The second spin echo 252 is phase-encoded using a phase-encoding gradient pulse 223 and slice-encoded using a slice-encoding gradient pulse 233 and is read out using a "read-out" gradient pulse 242. After read-out, the phase of the transverse magnetization is rewound using a phase rewinder gradient pulse 224 that has the same amplitude but negative polarity compared to the phase-encoding gradient pulse 223 and a slice rewinder gradient pulse 234 that has the same amplitude but negative polarity compared to the slice-encoding gradient 233. At a time interval, 2τ, after the second refocusing RF pulse 203, a third refocusing RF pulse 204 and slab-selective gradient pulse 214 cause the transverse magnetization to refocus a third time (corresponding spin echo not shown). Multiple additional refocusing RF pulses and read-out gradients are used to collect additional k-space encoded echoes during the TR.

The flip angles for the initial refocusing RF pulses 202, 203, 204 are shown decreasing in amplitude in accordance with an embodiment. The flip angle of constant width RF refocusing pulses is determined based on the pulse amplitude of the RF refocusing pulse. By decreasing the amplitudes (and therefore the flip angles) of the first refocusing RF pulses until a target signal level is achieved, a pseudo-steady state of magnetization may be achieved efficiently without the creation of signal oscillations and accompanying image artifacts. Although FIG. 2 shows selective refocusing RF pulses, non-selective (i.e., "hard") RF pulses may alternatively be used to decrease echo spacing and increase acquisition efficiency.

The multiple k-space encoded echoes 251, 252 that are collected in each TR are distributed into $k_y$ and $k_z$, such that the k-space lines collected from the echoes occurring with weighting closest to the desired TE are distributed into the center of k-space. The reconstructed image contrast will therefore be most strongly weighted by the desired TE. In one embodiment, k-space encoded echoes from successive TRs are distributed in $k_z$ by stepping the value of $k_z$ for each TR and distributed in $k_y$ by stepping the value of $k_y$ for each echo in the train. Alternatively, other k-space sampling strategies may be used including, but not limited to, projection acquisition, spiral sampling and circular sampling.

A spin preparation may be prepended to the pulse sequence shown in FIG. 2 to prepare the longitudinal magnetization in a desired state prior to excitation by the excitation RF pulse 201. Many types of spin preparations are compatible with a 3D FSE sequence, for example, a T2-weighting spin preparation, an inversion-recovery spin preparation, a fat suppression preparation, or a diffusion-weighting spin preparation. In an embodiment, at the end of the read-out, an additional refocusing RF pulse (not shown) may be played followed by a "fast recovery" or "driven equilibrium" tip up pulse (not shown) to return remaining transverse magnetization to the longitudinal direction and therefore accelerate T1 recovery.

In alternative embodiments, alternative pulse sequences that use a train of refocusing RF pulses may be substituted for the 3D FSE sequence described in FIG. 2. For example, a GRASE (i.e., "Gradient and Spin echo") pulse sequence may be used, in which multiple k-space lines are acquired after each refocusing RF pulse using an oscillating gradient waveform to create multiple gradient echoes in addition to the spin echo. Single Shot FSE (SSFSE) may also be used, in which a single 2D image is obtained for an echo train.

Figure 3:
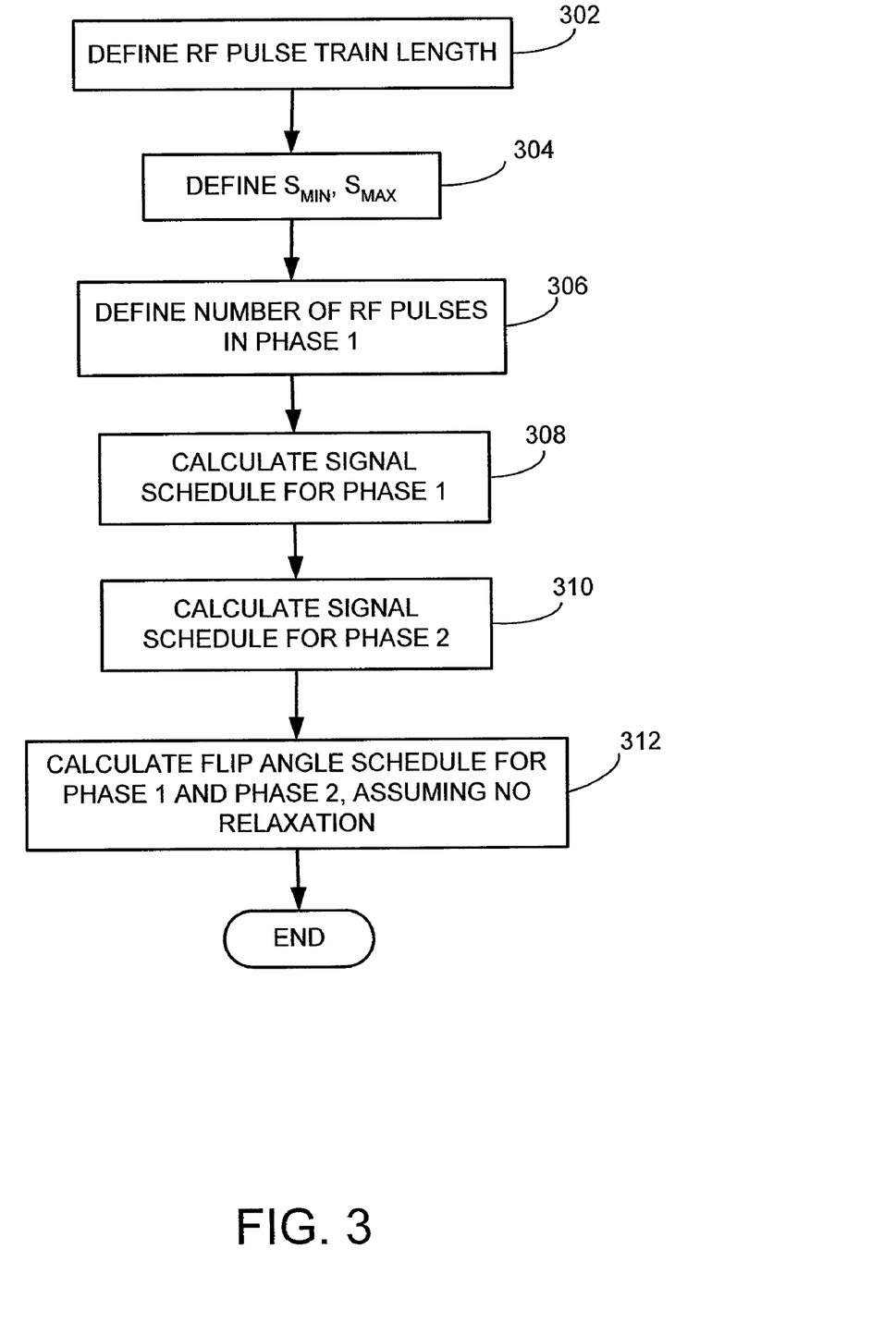
FIG. 3 is a flowchart illustrating a method for calculating a flip angle schedule for a train of refocusing RF pulses in accordance with an embodiment.

FIG. 3 is a flowchart illustrating a method for calculating a flip angle schedule for a train of refocusing RF pulses in accordance with an embodiment. A target signal schedule is calculated or defined and then the flip angle schedule is calculated from the target signals of the target signal schedule. The target signal schedule includes a target signal for each echo in the echo train. As mentioned above, the target signal schedule includes two phases. In a first phase, the target signals are defined so as to establish a psuedo-steady state. In a second phase, the target signals are increased monotonically for the remainder of the train of RF refocusing pulses. Alternatively, the target signal may reach a maximum value before the end of the echo train and remain at the maximum value for the remainder of the echo train. Referring now to FIG. 3, at block 302, the number of refocusing RF pulses in the RF pulse train is defined (e.g., by a MRI system operator) by specifying an "Echo Train Length" (ETL). Typically, the ETL is defined based on the number of k-space lines required in the y-direction to achieve a desired spatial resolution along the corresponding physical direction. For example, if a spatial resolution greater than 0.5 mm is desired for the physical direction corresponding to the logical y-axis and the Field of View (FOV) for that direction is 16 cm, then a minimum of 320 $k_y$ lines will be required to completely fill k-space along that direction. For a complete k-space filling scheme, setting ETL=320 acquires sufficient lines of $k_y$ to achieve this spatial resolution. For incomplete k-space filling schemes, it is possible to acquire fewer k-space lines. For example, in a homodyne reconstruction approach acquiring 60% of the $k_y$ lines, the ETL may be reduced to 192. Other incomplete k-space strategies, such as zero-filling and parallel imaging schemes may be used additionally or as an alternative. At block 304, a target minimum signal, $S_{min}$, and a target maximum signal, $S_{max}$ are defined, for example, automatically or by a system operator. Alternatively, a minimum flip angle, $\alpha_{min}$, and a maximum flip angle, $\alpha_{max}$ may be defined and $S_{min}$ and $S_{max}$ may be calculated from the minimum and maximum flip angles. The maximum and minimum target signals may be derived from the maximum and minimum refocusing RF pulse flip angles using the following equation:

$$s(\alpha) = (\sin\frac{\alpha}{2})^{\frac{1}{2}} P_{-\frac{1}{2}}\left[\sin\frac{\alpha}{2}\left(1 + \frac{\sin^2\alpha}{8\sin^4\frac{\alpha}{2}}\right)\right] \quad (1)$$

where P is a Legendre function. This equation assumes pseudo-steady state conditions and infinite relaxation times. At block 306, the number of refocusing RF pulses required to achieve a pseudo-steady state in the first phase of the target signal schedule (and therefore in the first phase of the flip angle schedule) is defined, for example, automatically or by the system operator.

At block 308, target signals are calculated or defined for the first phase of the target signal schedule for the RF pulse train. Preferably, the target signals for the first phase are calculated or defined such that $S_{min}$ is approached over several pulses. A pseudo-steady state of magnetization may be achieved even for very low flip angles (e.g. 30°) by approaching $S_{min}$ gradually as is known in the art. In a preferred embodiment, an asymptotic approach to $S_{min}$ may be used to bring the spin system rapidly into pseudo-steady state. Individual target signals, $S_n$, where n labels the RF pulse number, may be set using the following equations:

$$S_1 = \frac{1}{2}(1 + S_{min}) \quad (2)$$

$$S_n = \frac{1}{2}(S_{n-1} + S_{min}) \quad (3)$$

The first phase may include approximately 2-10 refocusing RF pulses to achieve pseudo-steady state conditions for very low flip angles. To minimize the echo time, the number of refocusing pulses in the first phase may be set equal to the echo number at which the center of k-space is sampled. Initial echoes may be discarded or the signal values adjusted to minimize the effect of the rapidly decreasing signal during this phase.

Figure 5:
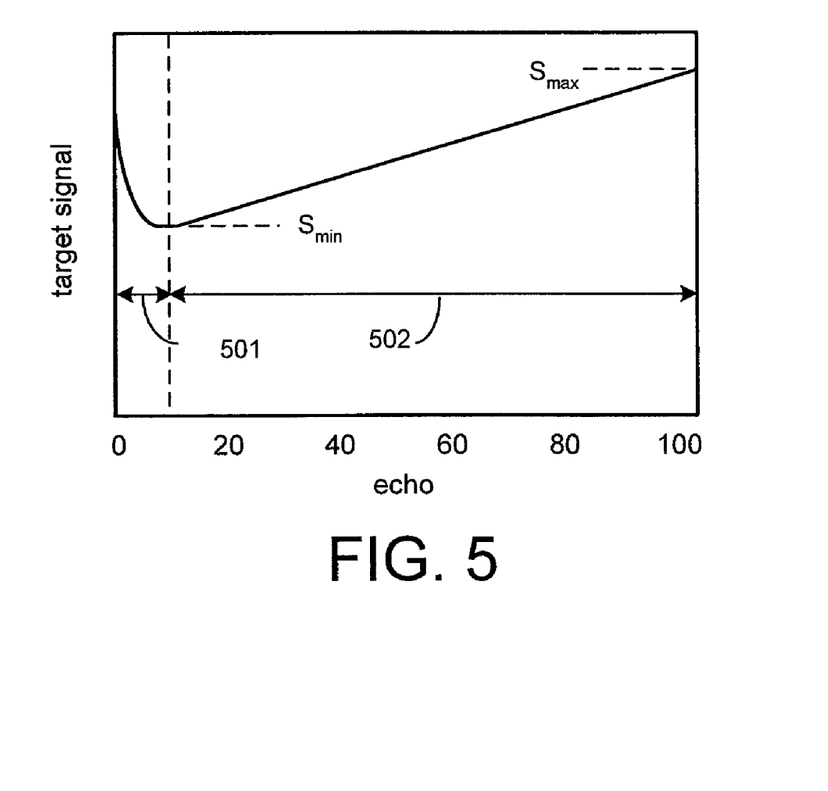
FIG. 5 shows an exemplary target signal schedule in accordance with an embodiment.
Figure 6:
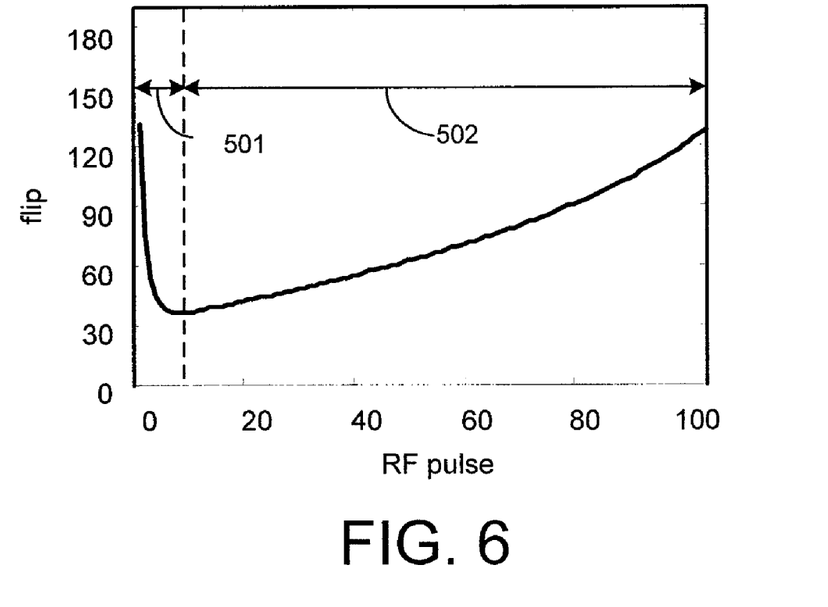
FIG. 6 shows an exemplary flip angle schedule corresponding to the target signal schedule shown in FIG. 5 in accordance with an embodiment.

At block 310, a target signal schedule for the second phase is calculated or defined. In the second phase, the target signal is increased monotonically to $S_{max}$. A simple monotonic increase in signal is provided using a linear increase from $S_{min}$ to $S_{max}$ for the second phase. FIG. 5 shows an exemplary target signal schedule in accordance with an embodiment. In FIG. 5, the target signal schedule shows an asymptotic approach to a minimum signal level, $S_{min}$, in a first phase 501 which establishes a pseudo-steady state of the magnetization at $S_{min}$. In a second phase 502 the target signal increases from $S_{min}$ to a maximum signal level, $S_{max}$. FIG. 6 shows an exemplary flip angle schedule corresponding to the target signal schedule shown in FIG. 5 in accordance with an embodiment. The flip angles are shown decreasing in the first phase 501 and increasing in the second phase 502.

Returning to FIG. 3, at block 312, a flip angle schedule for the first phase and the second phase is calculated, ignoring the effects of relaxation. The flip angles required to achieve the target signals for the RF pulses in Phase 1 may be calculated by inverting Equation 1. An approximation to an inverted form of Equation 1 may be derived using a polynomial expansion or other approximation technique. For example, a close approximation to an inverted form of Equation 1 is given by:

$$\alpha = 2\sin^{-1}(x^2) \quad (4)$$

where $x = -0.11917\ s^4 + 0.494707\ s^3 - 0.548777\ s^2 + 1.089704\ s + 0.084232$ As in Equation 1, this expression does not utilize tissue relaxation properties.

Figure 4:
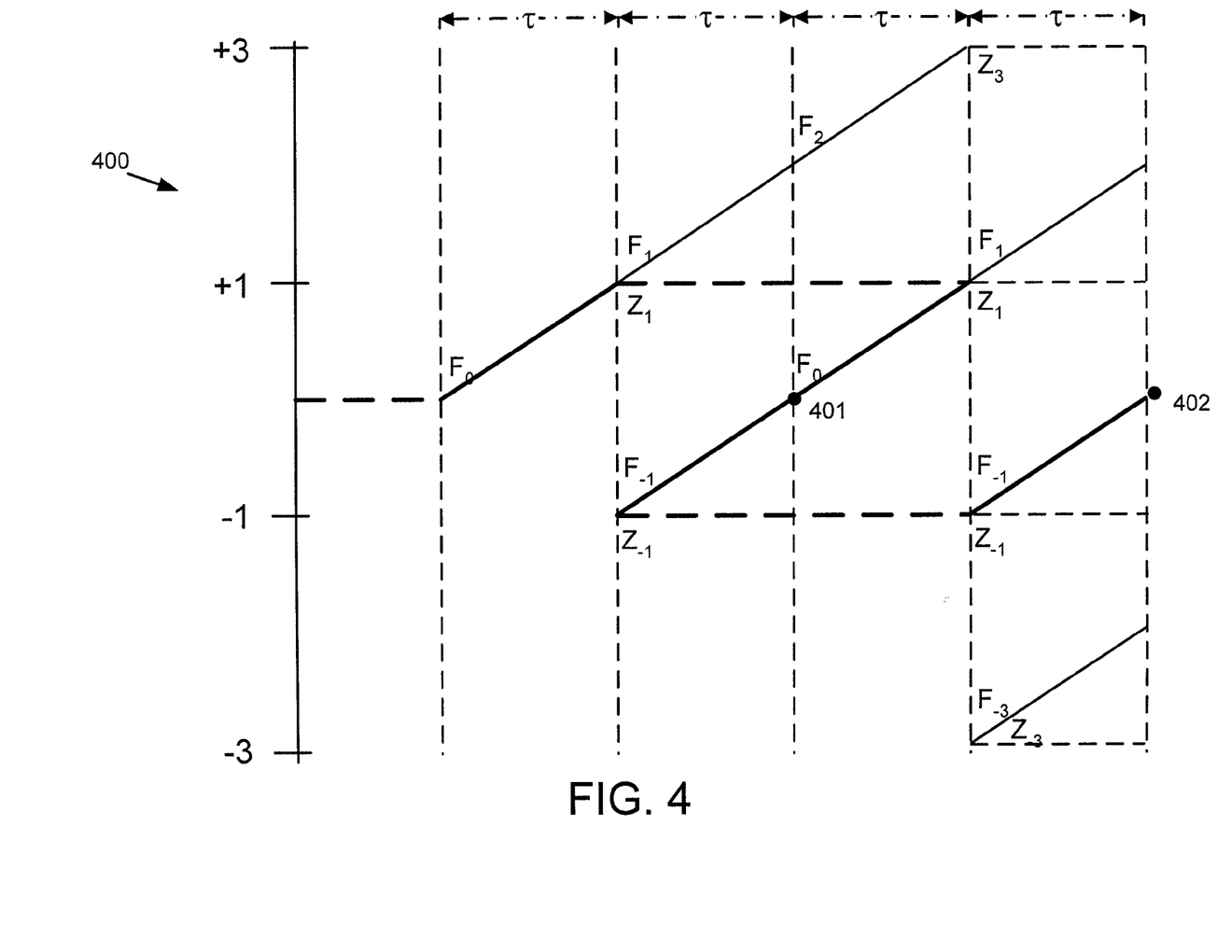
FIG. 4 shows an Extended Phase Graph (EPG) for a 2-echo Carr-Purcell-Meiboom-Gill echo train in accordance with an embodiment.

Alternatively, flip angles may be calculated from the target signals using an Extended Phase Graph (EPG) method that is modified to ignore relaxation. The EPG is a representation of the evolution of the spin system during the course of a pulse sequence. FIG. 4 shows an EPG for a 2-echo Carr-Purcell-Meiboom-Gill (CPMG) echo train in accordance with an embodiment. The graph 400 describes how longitudinal magnetization ("Z"), depicted by dashed lines, is converted by the 90° excitation pulse to transverse magnetization ("F"), depicted by solid lines, which is initially coherent but dephases over the period $\tau$. An RF pulse less than 180° can be considered to partition the spin system into components. Part of the transverse magnetization is inverted and this portion will rephase over the next period $\tau$ to form a spin echo 401 (with signal $s_1$). Part of the transverse magnetization continues to dephase and part is converted back to longitudinal magnetization where it does not dephase and relaxes according to T1 rather than T2. If the gradient area is consistent in every period $\tau$, then the longitudinal and transverse magnetization will converge just as the next RF pulse is applied. Accordingly, the number of configurations of the longitudinal and transverse magnetization is limited and may be described in terms of an integer configuration order k, denoted as subscripts of F and Z. A second echo 402 (with signal $s_2$) is a combination of spin and stimulated echo components, as will be any later echoes.

The EPG method may be applied to calculate the amount of magnetization in each longitudinal and transverse partition. For a CPMG sequence, magnetization is considered after it has been excited, when it is purely transverse and coherent:

$$F_k = \begin{cases} 1 & k = 0 \\ 0 & k \neq 0 \end{cases} \quad (5)$$

$$Z_k = 0$$

where $F_k$ is the $k^{th}$ order configuration of transverse magnetization and $Z_k$ is the $k^{th}$ order configuration of longitudinal magnetization. Nutation (due to RF pulses) and precession (due to gradients and off-resonance) affect the spin system. As mentioned above, the method is modified to ignore tissue relaxation. The effect of precession is to increase the order of all transverse configurations. The order of longitudinal coherences, which do not precess, remain fixed. In each partition k:

$$F'_k = F_{k-1}$$

$$Z'_k = Z_k \quad (6)$$

The effect of an RF pulse of nutation angle $\alpha$ is to "mix" configurations of equal absolute order as given by:

$$\begin{bmatrix} F_k \\ Z_k \end{bmatrix}' = \begin{bmatrix} \frac{1}{2}(1+\cos\alpha) & \frac{1}{2}(1-\cos\alpha) & \sin\alpha \\ -\frac{1}{2}\sin\alpha & \frac{1}{2}\sin\alpha & \cos\alpha \end{bmatrix} \begin{bmatrix} F_k \\ F_{-k} \\ Z_k \end{bmatrix} \quad (7)$$

Signal is derived only from the coherent ($0^{th}$ order) transverse magnetization which only exists at the echo, a period τ after each RF pulse.

$$s = F_0 \quad (8)$$

The signal after a given RF pulse can be traced back to the $1^{st}$ and $-1^{st}$ order partitions of magnetization prior to that pulse. To meet some target signal level $s_{target}$, the equation may be inverted to yield the nutation that will generate this signal level:

$$\alpha = 2\tan^{-1}\left(\frac{Z_1 + \sqrt{Z_1^2 - (F_1 - s_{target})(F_{-1} - s_{target})}}{F_1 - s_{target}}\right) \quad (9)$$

If the argument within the square-root is negative, a real solution does not exist, indicating the target signal can not be met. A maximum flip angle may be applied instead.

In summary, the modified EPG method may consist of the following steps:
1. Assert initial conditions (apply Eq. 5)
For each RF pulse and echo repeat:
2. precession (apply Eq. 6)
3. determine flip angle based on target signal (apply Eq 9)
4. nutation (apply Eq. 7)
5. precession (apply Eq. 6)
6. determine signal (apply Eq. 8)

Figure 7:
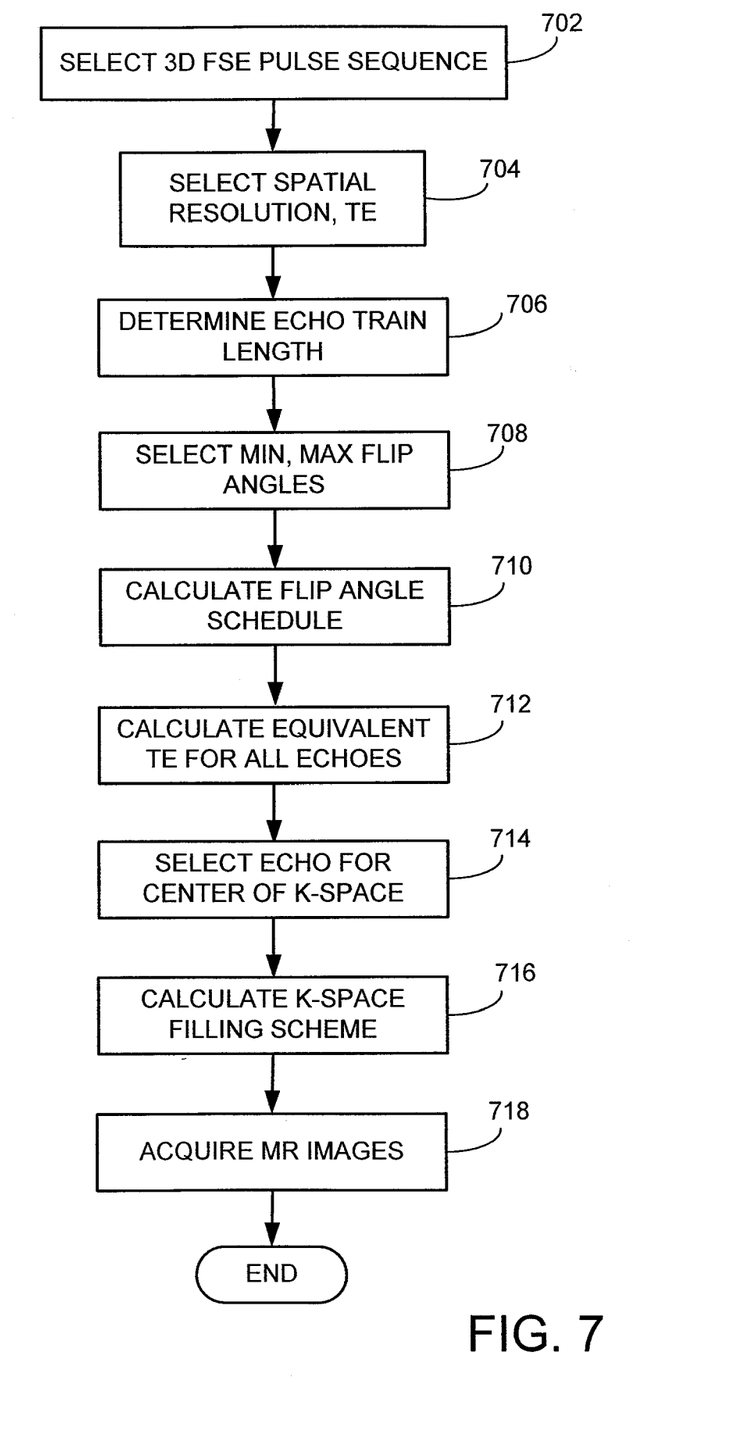
FIG. 7 is a flowchart illustrating a method for acquiring MR images using a 3D FSE pulse sequence in accordance with an embodiment.

A method for calculating a flip angle schedule for an echo train pulse sequence with reduced flip angles may be used, for example, with a 3D FSE pulse sequence to acquire images with T2-weighting while conforming to RF power deposition limits. FIG. 7 is a flowchart illustrating a method for acquiring MR images using a 3D FSE pulse sequence in accordance with an embodiment. At block 702, a system operator selects a 3D FSE pulse sequence for scanning a patient, for example, for scanning a patient's head. At block 704, the system operator selects a spatial resolution for all three orthogonal physical directions and selects an echo time based on the desired contrast weighting for the images. For example, an in-plane spatial resolution corresponding to a matrix of 256×256 elements may be desired and selected by the system operator and a TE=140 ms for moderate T2-weighting may be selected. At block 706, echo train length is determined, either by the system operator or automatically by the MRI system, for example, based on the spatial resolution specified at block 704. For example, given a full k-space filling with a 256×256 matrix size, an echo train length of 256 may be used. Nonselective refocusing RF pulses may be used to shorten the echo spacing. At block 708, the system operator selects a minimum flip angle by considering how likely motion and/or flow artifact will be for the anatomy selected for scanning and also selects a maximum flip angle. At block 710, the MRI system calculates a flip angle schedule according to the method described above with respect to FIG. 3.

At block 712, the MRI system calculates an equivalent TE, $TE_{equiv}$, for all the echoes in the echo train. The use of refocusing RF pulses with flip angles smaller than 180° results in the temporary storage of magnetization in stimulated echo coherence pathways which decay at the tissues' T1 relaxation rate instead of the T2 relaxation rate. This means that the appearance of the resulting images is less "T2-weighted" as compared to a 180° FSE readout when the same echo number is used to fill the center of k-space. Typically, a system operator selects a TE based on a desired contrast weighting appearance for the images. To achieve the desired contrast weighting when a train of refocusing RF pulses with flip angles smaller than 180° is used, a $TE_{equiv}$ may be calculated for each echo in the echo train. $TE_{equiv}$ describes the image contrast weighting that would be obtained if that echo were used to fill the center of k-space expressed in terms of an equivalent TE from a conventional T2-weighted sequence that uses only 180° refocusing pulses. Contrast weighting from a conventional sequence is more familiar to most system operators and the use of a $TE_{equiv}$ allows a system operator to select an image weighting as though he/she were prescribing a conventional sequence.

$TE_{equiv}$ may be calculated using the following method. Given a sequence of refocusing flip angles, signal (normalized for proton density, coil sensitivity, etc.) at each echo, s(n), may be regarded in terms of two separable functions, transverse coherence and relaxation:

$$s(n) = f_{coherence}(n) f_{relaxation}(n) \quad (10)$$

Ignoring relaxation, the signal may be computed using an Extended Phase Graph (EPG) method (that considers specific relaxation rates, T1 and T2) to produce the coherence term. The relaxation term may be determined for some representative material (e.g. $T1_{rep}=1000$ ms, $T2_{rep}=100$ ms) at each echo according to:

$$f_{relaxation}(n) = \frac{s(n)}{f_{coherence}(n)} \quad (11)$$

A $TE_{equiv}$ may be defined as the echo time that would achieve the same relaxation by T2 alone for the representative material used to compute the signal, s(n).

$$f_{relaxation}(n) = \exp\left(-\frac{TE_{equiv}(n)}{T2_{rep}}\right) \quad (12)$$

Solving for $TE_{equiv}$ yields the contrast-equivalent TE at each echo n.

$$TE_{equiv}(n) = -T2_{rep} \ln\left(\frac{s(n)}{f_{coherence}(n)}\right) \quad (13)$$

Figure 8:
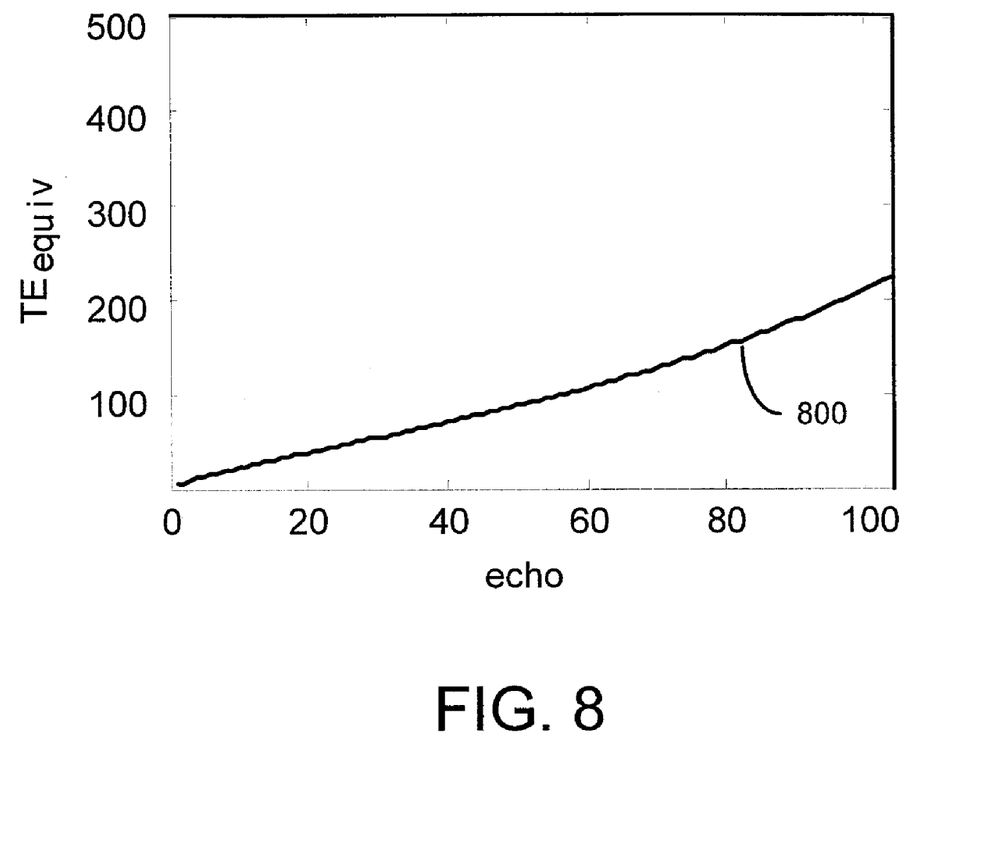
FIG. 8 shows exemplary effective TE values at each echo of an echo train corresponding to the flip angle schedule shown in FIG. 6 in accordance with an embodiment.

FIG. 8 shows exemplary effective TE values at each echo of an echo train corresponding to the flip angle schedule shown in FIG. 6 in accordance with an embodiment. Curve 800 illustrates effective TE values at each echo assuming echo spacing of 4.2 ms.

Returning to FIG. 7, at block 714, the MRI system selects the echo with the $TE_{equiv}$ closest to the TE value selected by the system operator at block 704. At block 716, the MRI system then calculates a k-space filling scheme based on positioning the selected echo at the center of k-space. For example, a linearly-ordered, full-Fourier phase encoding over 256 echoes may be calculated based on sampling the center of k-space at 585 ms at the $130^{th}$ echo for an equivalent TE=140 ms. For partial k-space linear filling schemes, initial echoes may be discarded in order to place the appropriate echo at the center of k-space. At block 718, the scanner operator initiates scanning of the patient using the pulse sequence defined at blocks 702-714.

Fast Spin Echo imaging with low refocusing flip angles is more susceptible to signal loss due to flow and motion than a similar acquisition using 180° refocusing RF pulses. This can be a problem for T2-weighted imaging of the brain and spine where cerebrospinal fluid (CSF) signal loss in areas of high flow is considered an image artifact. CSF flow is known to be caused by blood pressure variation in the head with periodicity equal to the cardiac cycle. In some embodiments, signal loss in CSF may be decreased by gating the echo train to the cardiac cycle to synchronize the portion of the RF pulse train with the lowest flip angles to the slowest period of CSF flow. The time at which the pulse train is executed with respect to the cardiac cycle may be chosen so that a maximum, or alternatively, a minimum, signal is generated by moving or flowing spins. Cardiac gating may be accomplished using ECG (electrocardiography) or plethysmograph sensors attached to the patient that send signals to an MRI system via, for example, a controller such as the physiological acquisition controller 44 shown in FIG. 1.

Computer-executable instructions for calculating a flip angle schedule for a train of refocusing RF pulses according to the above-described method may be stored on a form of computer readable media. Computer readable media includes volatile and nonvolatile, removable and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed either directly, or by internet or by other computer network forms of access.

This written description uses examples to disclose embodiments the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made without departing from the spirit thereof. The scope of these and other changes will become apparent from the appended claims.

I claim:

1. A method for calculating a flip angle schedule for a spin echo train with reduced refocusing flip angles, usable in magnetic resonance imaging, the spin echo train having a plurality of spin echoes, the method comprising:
defining a target signal schedule including target signals for each spin echo in the spin echo train, the target signal schedule comprising a first phase configured to establish a pseudo-steady state and a different, second phase subsequent to the first phase where each of the target signals increase from a pre-defined minimum signal value to a pre-defined maximum signal value; and
calculating a corresponding flip angle schedule from the target signal schedule using only non-relaxation properties wherein the calculated corresponding flip angle schedule is utilized in performing magnetic resonance imaging.

2. A method according to claim 1, wherein the first phase of the target signal schedule comprises target signals that decrease asymptotically to the pre-defined minimum signal value.

3. A method according to claim 1, wherein each of the target signals of the second phase of the target signal schedule increase from the pre-defined minimum signal value to the pre-defined maximum signal value.

4. A method for acquiring magnetic resonance images using a spin echo train with reduced refocusing flip angles, usable in magnetic resonance imaging, the spin echo train having a plurality of spin echoes, the method comprising:
applying a magnetic field to an imaging subject comprising tissues to cause a net longitudinal magnetization in the tissues;
defining a target signal schedule including target signals for each spin echo in the spin echo train, the target signal schedule comprising a first phase configured to establish a pseudo-steady state and a different, second phase subsequent to the first phase where each of the target signals increase from a pre-defined minimum signal value to a pre-defined maximum signal value;
calculating a corresponding flip angle schedule from the target signal schedule using only non-relaxation properties;
generating an excitation radio frequency pulse;
generating a plurality of refocusing radio frequency pulses, each refocusing radio frequency pulse having a flip angle determined based on the flip angle schedule; and
acquiring magnetic resonance imaging data from which magnetic resonance images are created.

5. A method according to claim 4, further comprising: calculating an equivalent TE for each spin echo in the spin echo train.

6. A method according to claim 5, further comprising: selecting a spin echo to fill a center line of k-space based on the equivalent TE of the spin echo.

7. A method according to claim 4, wherein the plurality of refocusing radio frequency pulses is generated in accordance with a single-shot fast spin echo (SSFSE) pulse sequence.

8. A method according to claim 4, wherein the plurality of refocusing radio frequency pulses is generated in accordance with a gradient and spin echo (GRASE) pulse sequence.

9. A method according to claim 4, wherein the plurality of refocusing radio frequency pulses is generated in accordance with a three-dimensional fast spin echo (3D-FSE) pulse sequence.

10. A method according to claim 4, wherein the plurality of refocusing radio frequency pulses is synchronized to a respiratory cycle.

11. A method according to claim 4, wherein the plurality of refocusing radio frequency pulses is synchronized to a cardiac cycle.

12. A non-transitory computer-readable medium having computer-executable instructions for performing a method for calculating a flip angle schedule for a spin echo train with reduced refocusing flip angles, the spin echo train having a plurality of spin echoes, the computer-readable medium comprising:
a non-transitory computer readable medium program code for defining a target signal schedule including target signals for each spin echo in the spin echo train, the target signal schedule comprising a first phase configured to establish a pseudo-steady state and a different, second phase subsequent to the first phase where each of the target signals increase from a pre-defined minimum signal value to a pre-defined maximum signal value; and a non-transitory computer readable medium program code for calculating a corresponding flip angle schedule from the target signal schedule using only non-relaxation properties, wherein the calculated corresponding flip angle schedule is utilized in performing magnetic resonance imaging.

13. An apparatus configured for acquiring magnetic resonance images using a spin echo train with reduced refocusing flip angles, the spin echo train having a plurality of spin echoes, the apparatus comprising:
- a magnetic resonance imaging assembly comprising a magnet, a plurality of gradient coils, a radio frequency coil, a radio frequency transceiver system, and a pulse generator module; and
- a computer system coupled to the magnetic resonance imaging assembly and programmed via a non-transitory computer readable medium program code to:
- define a target signal schedule including target signals for each spin echo in the spin echo train, wherein the target signal schedule comprising a first phase configured to establish a pseudo-steady state and a different, second phase subsequent to the first phase where each of the target signals increase from a pre-defined minimum signal value to a pre-defined maximum signal value;
- calculate a corresponding flip angle schedule from the target signal schedule using only non-relaxation properties;
- generate an excitation radio frequency pulse;
- generate a plurality of refocusing radio frequency pulses, each refocusing radio frequency pulse having a flip angle determined based on the flip angle schedule; and
- acquire magnetic resonance imaging data from which magnetic resonance images are created.

14. An apparatus according to claim 13, wherein the first phase of the target signal schedule comprises target signals that decrease asymptotically to the pre-defined signal value.

15. An apparatus according to claim 13, wherein each of the target signals of the second phase of the target signal schedule increase from the pre-defined minimum signal value to the pre-defined maximum signal value.

16. An apparatus according to claim 13, wherein the plurality of refocusing radio frequency pulses is generated in accordance with a single-shot fast spin echo (SSFSE) pulse sequence.

17. An apparatus according to claim 13, wherein the plurality of refocusing radio frequency pulses is generated in accordance with a gradient and spin echo (GRASE) pulse sequence.

18. An apparatus according to claim 13, wherein the plurality of refocusing radio frequency pulses is generated in accordance with a three-dimensional fast spin echo (3D-FSE) pulse sequence.

19. An apparatus according to claim 13, wherein the plurality of refocusing radio frequency pulses is synchronized to a respiratory cycle.

20. An apparatus according to claim 13, wherein the plurality of refocusing radio frequency pulses is synchronized to a cardiac cycle.

* * * * *